United States Patent [19]

Khavari

[11] Patent Number: 5,706,822
[45] Date of Patent: Jan. 13, 1998

[54] METHOD AND COMPUTER PROGRAM FOR CREATING INDIVIDUALIZED EXERCISE PROTOCOLS

[75] Inventor: Ali A. Khavari, New Britain, Conn.

[73] Assignee: Kozz Incorporated, Kansas City, Mo.

[21] Appl. No.: 630,860

[22] Filed: Mar. 29, 1996

[51] Int. Cl.⁶ .................................................. A61B 5/002
[52] U.S. Cl. ............................... 128/668; 128/707; 482/9
[58] Field of Search ........................... 128/668, 670, 128/700, 707; 364/413.01, 413.02, 413.04; 482/9, 901, 902

[56] References Cited

U.S. PATENT DOCUMENTS

| | | | |
|---|---|---|---|
| 4,828,257 | 5/1989 | Dyer et al. | 482/9 |
| 4,860,763 | 8/1989 | Schminke | 128/707 |
| 5,103,828 | 4/1992 | Sramek . | |
| 5,108,363 | 4/1992 | Tuttle et al. . | |
| 5,163,439 | 11/1992 | Dardik | 128/707 |
| 5,234,404 | 8/1993 | Tuttle et al. . | |
| 5,297,558 | 3/1994 | Acorn et al. . | |
| 5,410,472 | 4/1995 | Anderson | 482/9 |
| 5,474,090 | 12/1995 | Begun et al. | 128/707 |

Primary Examiner—Jennifer Bahr
Assistant Examiner—Bryan K. Yarnell
Attorney, Agent, or Firm—Hovey, Williams, Timmons & Collins

[57] ABSTRACT

A computer program and method for creating individualized exercise protocols for individuals recovering from various cardiovascular and/or pulmonary diseases is disclosed. The computer program includes receiving means for receiving health information relating to the individual; access means for accessing a plurality of patient data records, each of the patient data records including patient information and an exercise protocol for a patient who has previously completed rehabilitation; comparing means for comparing the health information with the patient data records and for identifying patient data records that contain patient information that is similar to the health information; and creating means for creating an exercise protocol for the individual based on the exercise protocols in the identified data records.

7 Claims, 3 Drawing Sheets

Microfiche Appendix Included
(2 Microfiche, 72 Pages)

METHOD AND COMPUTER PROGRAM FOR CREATING INDIVIDUALIZED EXERCISE PROTOCOLS

APPENDICES

A Source Code Appendix containing the source code of the computer program of the present invention and an Exercise Protocol Appendix containing an exemplary protocol are appended hereto, consisting of 2 microfiche and 72 pages, and are hereby incorporated by reference into this application as if fully set forth herein.

BACKGROUND OF THE INVENTION

1. Field of the Invention

The present invention relates to computer-readable storage devices for storing computer programs for operating computers. More particularly, the invention relates to a computer program and method for creating individualized exercise protocols for individuals recovering from various cardiovascular and/or pulmonary diseases.

2. Description of the Prior Art

Heart disease is the leading cause of death in the United States. Exercise training has been proven to reduce coronary heart disease risk and improve the quality of life of patients suffering from heart disease. Thus, the creation and monitoring of exercise protocols is the cornerstone of cardiopulmonary rehabilitation programs.

Prior art methods and programs for creating and monitoring exercise protocol s suffer from several limitations that limit their effectiveness. For example, one prior art exercise program directs patients to perform certain exercises for a pre-determined number of weeks or sessions. The patients begin the exercise protocol at a lower level than their desired goal and then gradually progress until the end of the pre-determined number of weeks or sessions. All of the patients perform basically the same exercise protocol for the same number of weeks or sessions regardless of their age, health, and other vital information. Unfortunately, these prior art programs often lead to a high attrition rate and do not effectively rehabilitate all patients because they do not take into account specific information about each patient performing the exercise protocol.

Another type of prior art exercise program directs patients to perform certain exercises for an indefinite amount of time until they reach their desired goals. These types of programs also often lead to a high attrition rate and do not effectively rehabilitate all patients because they cannot predict when the patients will complete the program or whether the program is even improving the patients' condition. Moreover, the patients often become discouraged because they are given few concrete goals to strive for.

A more particular limitation of prior art exercise programs is that they are not outcome based. Particularly, prior art exercise programs merely follow random timelines and pre-selected exercise regimens without taking into account the outcomes of other patients that have successfully undergone similar exercise rehabilitation.

Another limitation of prior art exercise programs is that they merely prescribe certain exercises but do not provide an effective means for monitoring the performance of the exercises to insure that the patients achieve their desired goals.

Another limitation of prior art exercise programs is that they fail to provide means for allowing a plurality of people such as doctors, rehabilitation therapists, billing personnel and others to monitor the performance of the exercise protocol.

OBJECT AND SUMMARY OF THE INVENTION

In view of the foregoing, it is an object of the present invention to provide an improved method and computer program for creating individualized exercise protocols for individuals recovering from cardiovascular and/or pulmonary diseases.

It is a more particular object of the present invention to provide a method and computer program for creating individualized exercise protocols that take into account specific information about each patient performing the exercise protocol.

It is another object of the present invention to provide a method and computer program for creating individualized exercise protocols that takes into account the outcomes of other patients that have previously undergone similar exercise rehabilitation.

It is another object of the present invention to provide a method and computer program for creating individualized exercise protocols that can direct a computer to control exercise machines for assuring that patients using the exercise machines will achieve their desired level of exercise.

It is another object of the present invention to provide a method and computer program for creating individualized exercise protocols that permits a plurality of people such as doctors, rehabilitation therapist, billing personnel and others to monitor the performance of the exercise protocols.

In view of these objects and other objects that become evident from the description of the preferred embodiments of the invention herein, an improved method and computer program for creating individualized exercise protocols is provided. The preferred method is implemented with the aid of a computer program stored on a computer-readable memory device for directing a computer. The computer program broadly includes receiving means for receiving health information relating to the individual; access means for accessing a plurality of patient data records, each of the patient data records including patient information and an exercise protocol for a patient who has previously completed rehabilitation; comparing means for comparing the health information with the patient data records for identifying patient data records that contain patient information that is similar to the health information; and creating means for creating an exercise protocol for the individual based on the exercise protocols in the identified data records.

In more detail, the preferred method begins when a doctor or therapist measures and/or determines certain health information for a patient including the patient's age, sex, heart rate, and blood pressure. A complete listing of the measured health information is set forth in the Detailed Description below.

This health information is then entered into the computer for use in creating an individualized exercise protocol for the individual. Advantageously, the computer program includes a medical database containing data records for a plurality of patients who have previously undergone exercise rehabilitation for recovery from cardiovascular and/or pulmonary diseases. Each of the data records includes health information for a patient, the exercise protocol prescribed for the patient, and the outcome of the rehabilitation program.

The computer program compares the health information for the current patient with the data records in the database for identifying data records containing similar health information. The computer program then creates an exercise protocol for the current patient based on the exercise protocols in the identified data records.

This method for creating exercise protocols is much more effective than prior art methods because each exercise protocol is automatically individualized for a particular patient by taking into account that patient's unique health information. Thus, numerous patients with various different health conditions and personal statistics are not subjected to the same generic exercise protocol.

Additionally, the present method provides for outcome based rehabilitation because each patient's exercise protocol is created by taking into account successful exercise protocols for previous patients with similar health information. Once the current patient successfully completes the exercise protocol, his or her health information, exercise protocol, and outcomes are stored as a new data record in the database for use in creating future patients' exercise protocols.

In preferred forms, the computer program directs the computer to control exercise machines electronically coupled with the computer. This allows the computer to control the operation of the exercise machines in accordance with the prescribed exercise protocols for assuring that the patients correctly use the exercise machines and therefore achieve their desired level of exercise. The computer may also be coupled with heart monitors, blood pressure monitors, and other portable vital statistic monitors for receiving vital statistics from the patients while the patients are performing the exercises called for in the exercise protocols.

The computer in which the computer program is stored my alsobe coupled with other remote computers and monitors by a conventional network for permitting a plurality of people such as doctors, rehabilitation therapists, billing personnel and others to monitor the performance of the exercise protocols.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENTS

Figure 1:
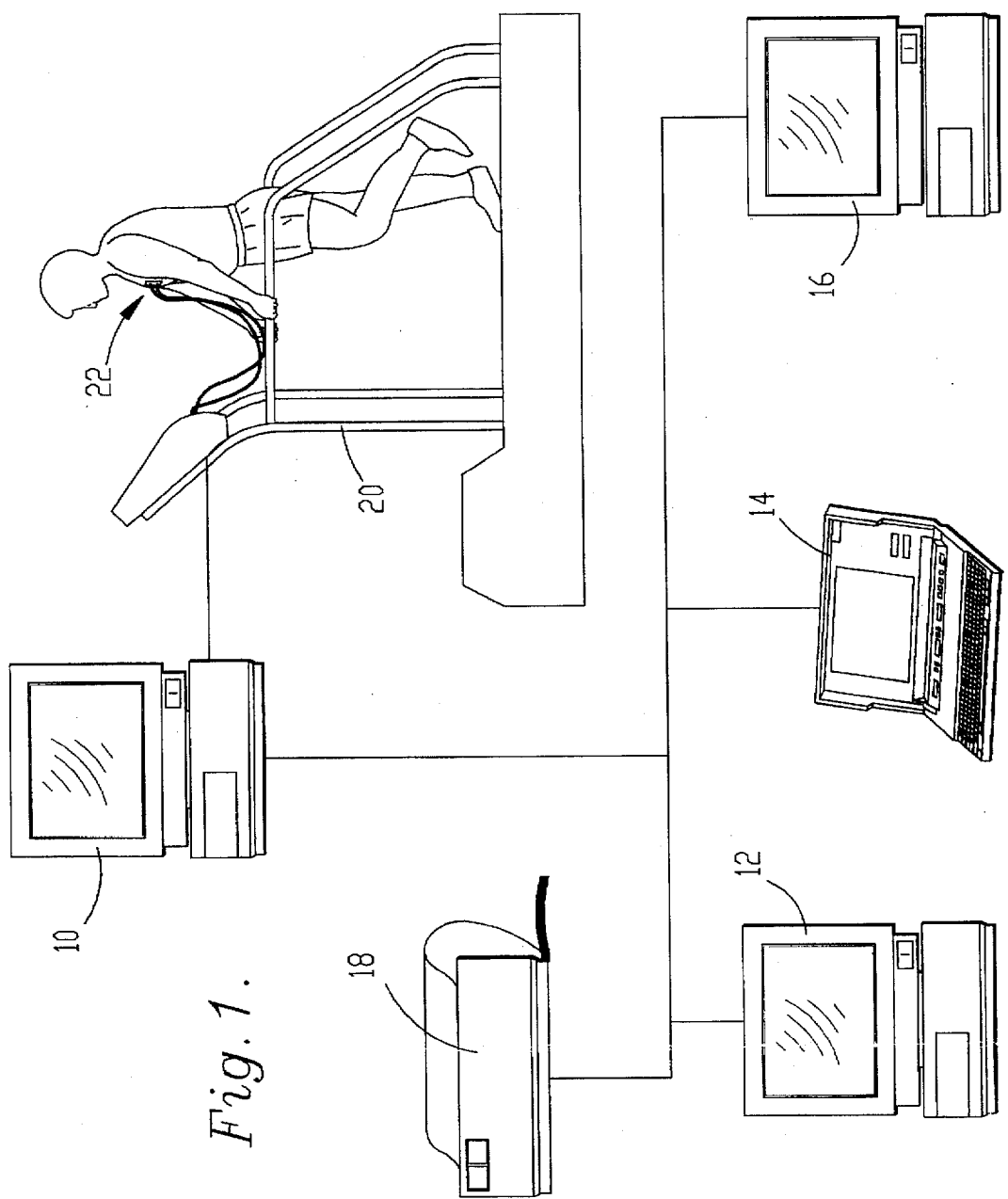
FIG. 1 is a schematic diagram of the computer hardware of the present invention including the computer for running or operating the computer program of the present invention.

As illustrated in FIG. 1, the computer program of the present invention is preferably stored or loaded into a personal computer 10 for directing the computer 10 to create individualized exercise protocols for individuals recovering from various cardiovascular and/or pulmonary diseases. The preferred computer 10 is an IBM compatible or equivalent microcomputer or laptop computer having an Intel 486, Pentium or its equivalent microprocessor. The computer 10 preferably includes a conventional 400 MB or larger internal hardrive, 8 MB or larger of RAM, a 3.5" and/or a CD drive, magnetic tape backup, and an internal or external fax/modem. Those skilled in the art will appreciate that the computer program may also be loaded in other conventional microprocessor driven devices including hand-held computer devices.

The computer 10 is preferably coupled to other computers and monitors by a conventional network 11 such as a LAN, WAN or phone connection for permitting others to monitor the performance of the exercise protocol. For example, the computer 10 may be coupled with a monitor 12 in a rehabilitation area, a laptop computer 14 in a doctor's office, a computer 16 in a billing and insurance office, and a printer 18.

The computer 10 may also be coupled with conventional electronic exercise machines 20 such as a treadmill, a stationary bicycle or a stair machine. The computer program is preferably operable for directing the computer 10 to control these exercise machines 20 for ensuring that the exercise machines 20 are operated in accordance with the created exercise protocols. Additionally, the computer 10 may also be coupled with portable vital statistic monitors 22 fastened to a patient such as a heart monitor or blood pressure monitor for receiving vital statistics from the patient while the patient is performing the exercises called for in the exercise protocol.

The computer program of the present invention is stored on a computer-readable memory device such as a floppy disk, compact optical disk, tape, or the computer's hard drive and is operable for directing the computer 10 to create individualized exercise protocols. The computer program may be written in any conventional computer language. The source code for the computer program is reproduced in its entirety in the attached Source Code Appendix and is described herein with reference to the flow charts illustrated in FIGS. 2 and 3.

In the method of the present invention, a doctor or therapist first measures and/or determines certain health information for the patient. This health information is measured and determined in a conventional manner and includes the following 32 variables:

(1) Patient's date of birth;
(2) Patient's age;
(3) Patient's sex (male or female);
(4) Patient's diagnostic;
(5) Patient's rest heart rate (RHR)
(6) Patient's rest systolic blood pressure (RSHR or RSBP);
(7) Patient's rest diastolic blood pressure (RDBP or RDHR);
(8) Name or method of the test protocol used to increase the patient's heart rate;
(9) Number of minutes the patient was executing or implementing the test protocol;
(10) Reason for the patient stopping the test;
(11) Patient's maximum heart rate (MHR);
(12) Patient's maximum systolic blood pressure (MSBP or MSHR);
(13) Patient's maximum diastolic blood pressure (MDHR or MDBP);
(14) Leg discomfort status (none, mild or severe);
(15) Does the patient receive beta blockers medicine (yes or no);
(16) Does the patient receive calcium channel blockers medicine (yes or no);
(17) Percent of patient's blood oxygen level (Sa02);
(18) Patient's hemoglobin (HGB);
(19) Patient's forced vital capacity (FVC);
(20) Patient's forced expiratory volume (FEV1);

(21) Patient's high density lipoprotein (HDL);

(22) Patient's low density lipoprotein (LDL);

(23) Patient's total cholesterol;

(24) Patient's triglyceride;

(25) Percent of patient's body fat;

(26) Patient's weight;

(27) Patient's height;

(28) Does the patient have any abnormalities or defect (yes or no);

(29) Patient's abnormalities or defect, if any;

(30) Today's date;

(31) Patient's first, middle and last name; and

(32) Patient's social security number.

Figure 2:
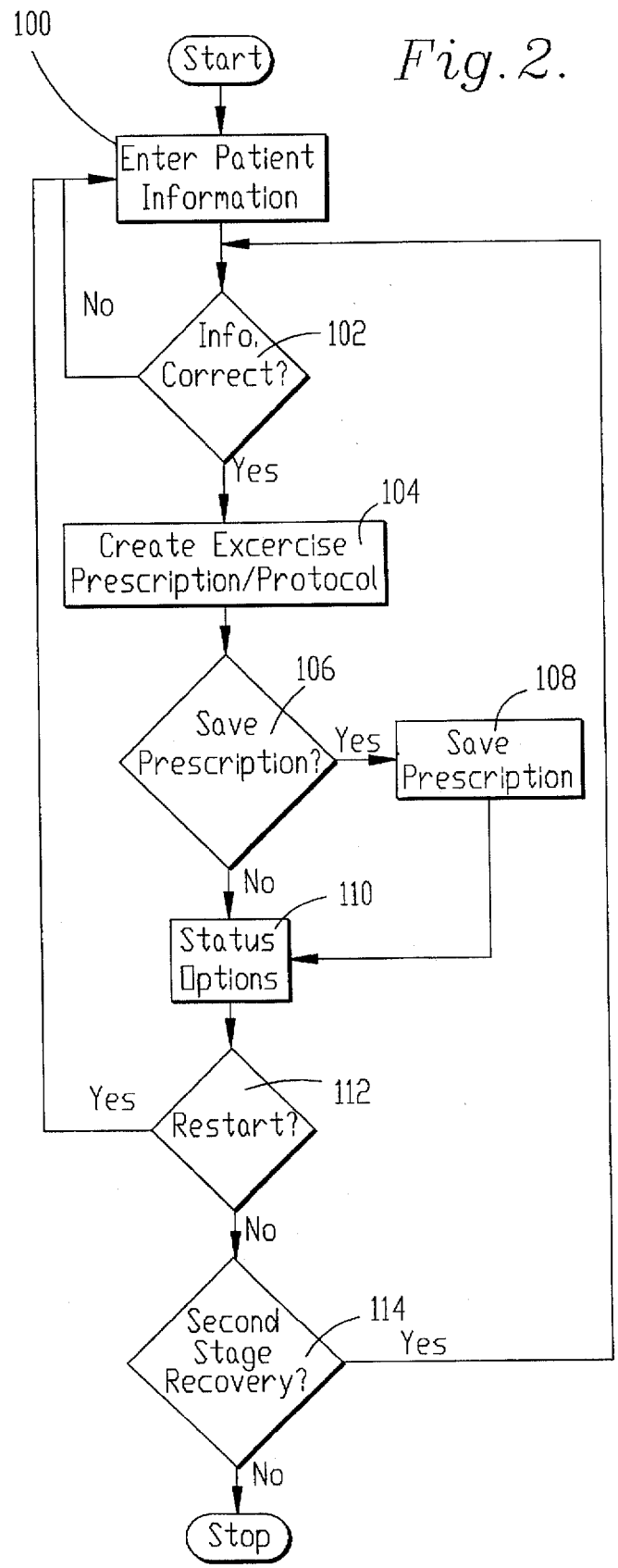
FIG. 2 is a flow chart illustrating the steps performed by the computer program and method of the present invention.

Referring to FIG. 2, the computer program begins at step 100 which prompts the operator to enter this health information into the computer 10. Step 102 then asks the operator to verify the correctness of the information. If the information was entered incorrectly, the program returns to step 100 to allow the operator to correct the information. However, if the information was entered correctly, the program proceeds to step 104.

Step 104 creates an exercise protocol for the patient by taking into account the entered health information. This step of the computer program and method is discussed in more detail below with reference to FIG. 3.

Once the exercise protocol has been created, step 106 asks whether the operator wishes to save the protocol. If the operator selects "no", the program proceeds directly to step 110. However, if the operator selects "yes", step 108 saves the exercise protocol as a patient data record in a medical database described below. The program then proceeds to step 110.

Step 110 lists several status options for continuing the method. For example, step 110 may allow the operator to restart the system to enter new patient information or enter "second stage recovery" as described below.

Step 112 asks whether the operator selected the restart option in step 110. If the answer to step 112 is "yes", the program returns to step 100 to prompt for the entry of new patient information. If the answer to step 112 is "no", the program proceeds to step 114.

Step 114 asks whether the operator selected the "second stage recovery" option in step 110. "Second stage recovery" is when a patient is being fetested after a given phase during his recovery. For example, after a patient has completed several exercise sessions, his or her ability to perform certain exercises may increase. The "second stage recovery" option allows the operator to create a new or modified exercise protocol based on the patient's improved physical condition. This new exercise protocol can be stored along with the patient's first exercise protocol in the patient's data record. As described in more detail below, this provides additional information that can be retrieved when creating and updating other patients' exercise protocols. If the answer to step 114 is "no", the program either returns to step 110 or ends.

Figure 3:
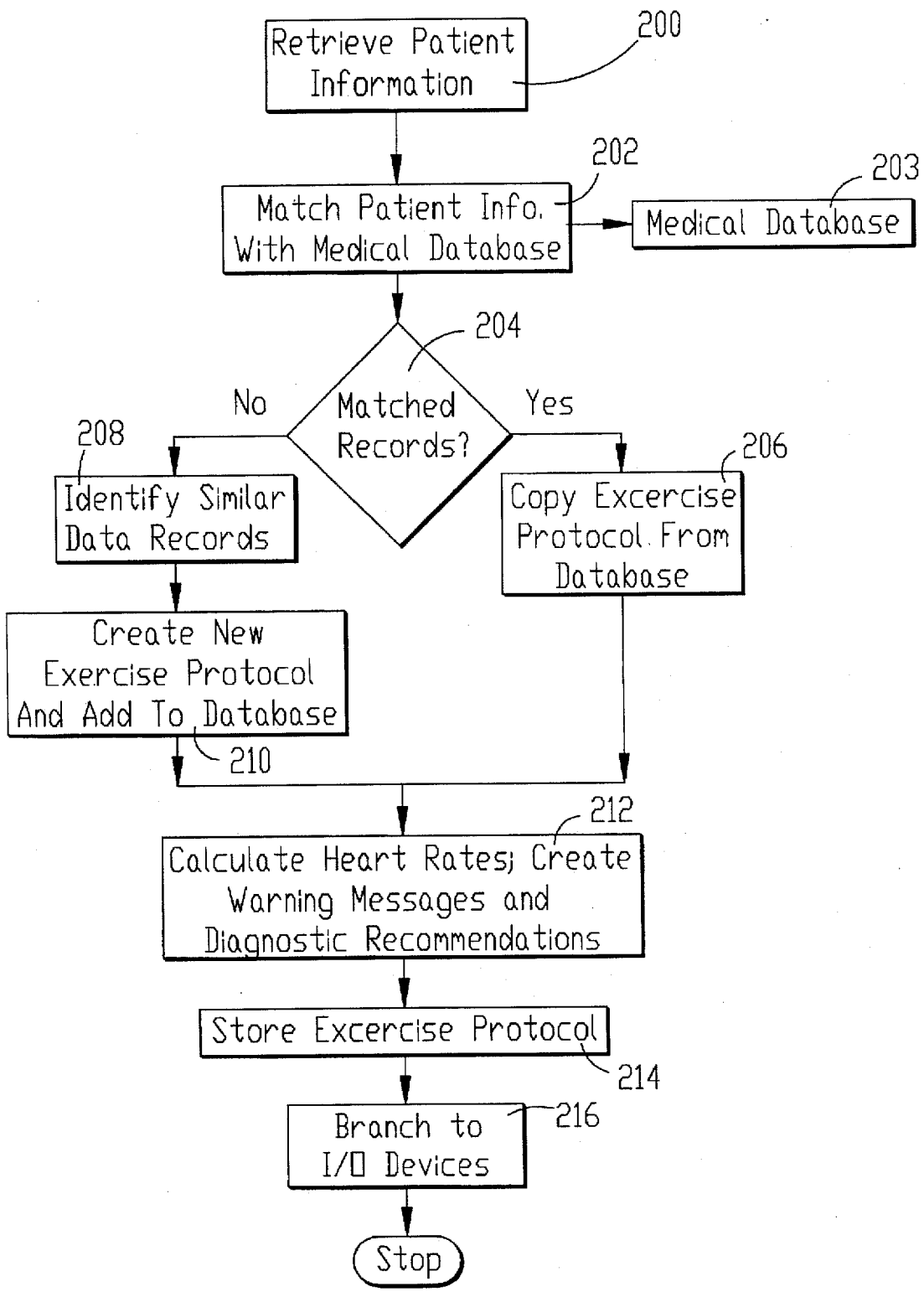
FIG. 3 is a continuation of the flow chart illustrated in FIG. 2.

FIG. 3 illustrates the steps taken to create an exercise protocol in more detail. This portion of the computer program begins at step 200 which retrieves the patient information entered in the above-described steps. Step 202 then attempts to match this entered patient information with data records for patients who have previously successfully performed exercise protocols during rehabilitation from cardiovascular and/or pulmonary diseases.

Advantageously, the computer program either includes a medical database 203 or has means for accessing a medical database that contains data records for a plurality of patients who have previously undergone exercise rehabilitation for recovery from cardiovascular and/or pulmonary diseases. Each of the data records in the database includes health information for a patient, the exercise protocol prescribed for the patient, and the outcome of the rehabilitation program. The health information includes the same 32 health variables listed above. The data records may also include additional information useful in prescribing an exercise protocol for a patient.

Step 202 compares the health information entered for the patient with the data records in the database to determine if the patient has an existing data record in the database. Step 204 then asks whether an exact match was found in step 202. If the answer is "yes", step 206 copies or duplicates the exercise protocol from the medical database and then proceeds to step 212.

However, if the answer to step 204 is "no", step 208 identifies data records in the database that contain health information that is similar to the 32 variables entered for the current patient or individual. The program then creates an exercise protocol for the current patient based on the exercise protocols in these identified data records.

This provides for outcome based rehabilitation because each patient's exercise protocol is created by taking into account successful exercise protocols for previous patients with similar health information. Once the current patient successfully completes the exercise protocol, his or her health information, exercise protocol, and outcomes are stored as a data record in the database for use in creating future patients' exercise protocols.

In the preferred embodiment, step 208 of the computer program identifies the two data records in the medical database that contain health information that is the most similar to the entered health information. To determine which data records are the most similar, the computer program considers the similarity of the 32 variables set forth above. The weighting of the 32 variables is set forth in detail in the attached Source Code Appendix.

Step 210 then takes these two identified data records and averages their exercise protocols for creating the exercise protocol for the current patient. For example, if the exercise protocol for one of the identified data records calls for two minutes of a particular exercise and the exercise protocol for the other of the identified data records calls for four minutes of the same exercise, step 210 creates a new exercise protocol that calls for three minutes of that particular exercise. The specific equations for calculating the new exercise protocol are conventional and are set forth in the attached Source Code Appendix.

Once an existing exercise protocol has been retrieved in step 206 or a new exercise protocol has been created in step 210, the program proceeds to step 212 which calculates the recommended exercise and rest heart rates for the patient while performing the exercises in the exercise protocol. Step 212 also adds warning messages and diagnostic recommendations. For example, if the system or software determines that the patient has difficulty reaching the recommended heart rate during early levels of the exercise protocol, this is noted in the exercise protocol. Similarly, if the system or software determines that the patient may demonstrate respiratory problems or dizziness during exercise, this is also noted.

Step 214 then stores the exercise protocol into a buffer or the medical database 203 and makes the exercise protocol available for editing, and/or viewing. Since all new exercise protocols are stored in the medical database 203, the database 203 becomes more comprehensive with each use. Thus, each exercise protocol that is created factors in more information than the previously created exercise protocols. Those skilled in the art will appreciate that this significantly improves the customization of the exercise protocols.

An example of an exercise protocol for a patient is set forth in the attached Exercise Protocol Appendix.

The exercise protocol includes the patient's vital statistics as well as the recommended exercise prescription. The exercise protocol also includes the warning messages discussed above.

Once the exercise protocol has been created and stored, the program proceeds to step 216 for branching to various input and output devices. For example, the exercise protocol can be viewed on the computer 10, or transmitted to monitor 12, the laptop computer 14, the computer 16 or the printer 18 via the network 11 as illustrated in FIG. 1.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A computer program stored on a computer-readable memory device for directing a computer to create an exercise protocol for an individual, the computer program comprising:

receiving means for receiving health information relating to the individual;

access means for accessing a plurality of patient data records, each of the patient data records including patient information and an exercise protocol for a patient who has previously completed rehabilitation;

comparing means for comparing the health information with the patient data records and for identifying patient data records that contain patient information that is similar to the health information; and creating means for creating an exercise protocol for the individual based on the exercise protocols in the identified data records;

the comparing means including means for identifying a two patient data records from patients other than the individual that include patient information that is closest to the health information.

2. The computer program as set forth in claim 1, the creating means including averaging means for averaging the exercise protocols from the two or more closest patient data records for creating the individual's exercise protocol.

3. The computer program as set forth in claim 2, including storing means for storing the individual's exercise protocol with the patient data records.

4. The computer program as set forth in claim 1, the health information and the patient information being selected from the group consisting of a patient's date of birth, a patient's age, a patient's sex, a patient's diagnostic, a patient's rest heart rate, a patient's rest systolic blood pressure, a patient's rest diastolic blood pressure, a method of the test protocol used to increase the patient's heart rate, a number of minutes the patient was executing or implementing the test protocol, a reason for the patient stopping the test, a patient's maximum heart rate, a patient's maximum systolic blood pressure, a patient's maximum diastolic blood pressure, a leg discomfort status of the patient, whether the patient receives beta blockers medicine, whether the patient receive calcium channel blockers medicine, a percent of patient's blood oxygen level, a patient's hemoglobin, a patient's forced vital capacity, a patient's forced expiratory volume, a patient's high density lipoprotein, a patient's low density lipoprotein, a patient's total cholesterol, a patient's triglyceride, a percent of patient's body fat, a patient's weight, a patient's height, whether the patient has any abnormalities or defect, a patient's abnormalities or defect, a current date, a patient's first, middle and last name; and a patient's social security number.

5. A method of creating a customized exercise protocol for an individual with the aid of a computer, the method comprising the steps:

receiving health information relating to the individual into the computer;

accessing a plurality of patient data records with the computer, each of the patient data records including patient information and an exercise protocol for a patient who has previously completed rehabilitation;

comparing the health information with the patient data records in the computer;

identifying patient data records that contain patient information that is similar to the health information; and creating an exercise protocol in the computer for the individual based on the exercise protocols in the identified data records;

the identifying step including identifying two patient data records from patients other than the individual that include patient information that is closest to the health information.

6. The computer program as set forth in claim 5, the creating means including averaging means for averaging the exercise protocols for the two closest patient data records for creating the individual's exercise protocol.

7. The computer program as set forth in claim 6, including storing means for storing the individual's exercise protocol with the patient data records.

* * * * *